(12) United States Patent
Subramanian et al.

(10) Patent No.: US 10,820,838 B2
(45) Date of Patent: Nov. 3, 2020

(54) SYSTEM FOR DETERMINING VESSEL SIZE USING LIGHT ABSORPTION

(71) Applicant: Briteseed LLC, Chicago, IL (US)

(72) Inventors: Hariharan Subramanian, Mundelein, IL (US); Jonathan Gunn, Chicago, IL (US); Amal Chaturvedi, Chicago, IL (US)

(73) Assignee: Briteseed, LLC, Chicago, IL (US)

( * ) Notice: Subject to any disclaimer, the term of this patent is extended or adjusted under 35 U.S.C. 154(b) by 277 days.

(21) Appl. No.: 15/551,276

(22) PCT Filed: Feb. 19, 2016

(86) PCT No.: PCT/US2016/018798
§ 371 (c)(1),
(2) Date: Aug. 15, 2017

(87) PCT Pub. No.: WO2016/134327
PCT Pub. Date: Aug. 25, 2016

(65) Prior Publication Data
US 2018/0042522 A1  Feb. 15, 2018

Related U.S. Application Data

(60) Provisional application No. 62/118,429, filed on Feb. 19, 2015.

(51) Int. Cl.
*A61B 5/107* (2006.01)
*A61B 5/024* (2006.01)
(Continued)

(52) U.S. Cl.
CPC .......... *A61B 5/1076* (2013.01); *A61B 5/0205* (2013.01); *A61B 5/02007* (2013.01);
(Continued)

(58) Field of Classification Search
CPC ..... A61B 5/0176; A61B 5/489; A61B 5/2007; A61B 5/1455–14552; A61B 5/1459;
(Continued)

(56) References Cited

U.S. PATENT DOCUMENTS

| 5,129,400 A | 7/1992 | Makino et al. |
| 5,259,761 A | 11/1993 | Schnettler et al. |

(Continued)

FOREIGN PATENT DOCUMENTS

| EP | 2 353 534 | 8/2011 |
| GB | 1 445 678 | 8/1976 |

(Continued)

OTHER PUBLICATIONS

C. Lee, H. S. Shin, J. Park and M. Lee, "The Optimal Attachment Position for a Fingertip Photoplethysmographic Sensor With Low DC," in IEEE Sensors Journal, vol. 12, No. 5, pp. 1253-1254, May 2012. doi: (Year: 2012).*

(Continued)

*Primary Examiner* — Bo Joseph Peng
(74) *Attorney, Agent, or Firm* — Cook Alex Ltd.

(57) ABSTRACT

A surgical system used to determine a size of a vessel within a region proximate to a working end of a surgical instrument includes at least one light emitter disposed at the working end of the surgical instrument, and at least one light sensor disposed at the working end of the surgical instrument opposite the at least one light emitter, the at least one light sensor adapted to generate a signal comprising a first pulsatile component and a second non-pulsatile component. The system also includes a controller coupled to the at least one light sensor, the controller comprising a splitter to separate the first pulsatile component from the second non-pulsatile component and an analyzer to quantify the size of the vessel within the region proximate to the working end (Continued)

of the surgical instrument based on the first pulsatile component.

16 Claims, 6 Drawing Sheets

(51) Int. Cl.
*A61B 5/1459* (2006.01)
*A61B 5/02* (2006.01)
*A61B 5/00* (2006.01)
*A61B 5/0205* (2006.01)
*A61B 5/1455* (2006.01)
*A61B 17/00* (2006.01)

(52) U.S. Cl.
CPC ...... *A61B 5/02028* (2013.01); *A61B 5/02416* (2013.01); *A61B 5/1079* (2013.01); *A61B 5/1459* (2013.01); *A61B 5/14551* (2013.01); *A61B 5/6847* (2013.01); *A61B 5/7214* (2013.01); *A61B 5/6884* (2013.01); *A61B 2017/00057* (2013.01)

(58) Field of Classification Search
CPC ... A61B 5/1473; A61B 5/0059; A61B 5/0062; A61B 5/0082–0086; A61B 5/02028; A61B 5/6847; A61B 5/1079; A61B 5/7214; A61B 5/14551; A61B 5/02416; A61B 5/02007; A61B 5/0205; A61B 5/1076; A61B 5/6884; A61B 2017/00057
See application file for complete search history.

(56) References Cited

U.S. PATENT DOCUMENTS

| | | | |
|---|---|---|---|
| 5,762,609 A | | 6/1998 | Benaron et al. |
| 5,769,791 A | * | 6/1998 | Benaron .............. A61B 5/0084 600/473 |
| 5,772,597 A | | 6/1998 | Goldberger et al. |
| 5,785,658 A | | 7/1998 | Benaron et al. |
| 5,807,261 A | | 9/1998 | Benaron et al. |
| 5,987,346 A | | 11/1999 | Benaron et al. |
| 6,178,340 B1 | | 1/2001 | Svetliza |
| 6,374,128 B1 | | 4/2002 | Toida et al. |
| 6,569,104 B2 | | 5/2003 | Ono et al. |
| 6,594,518 B1 | | 7/2003 | Benaron et al. |
| 6,922,577 B2 | | 7/2005 | Nakashima et al. |
| 7,006,861 B2 | | 2/2006 | Flock et al. |
| 7,112,201 B2 | | 9/2006 | Truckai et al. |
| 7,235,072 B2 | | 6/2007 | Sartor et al. |
| 7,515,265 B2 | | 4/2009 | Alfano et al. |
| 7,740,591 B1 | | 6/2010 | Starr et al. |
| 7,749,217 B2 | | 7/2010 | Podhajsky |
| 7,904,138 B2 | | 3/2011 | Goldman et al. |
| 7,983,738 B2 | | 7/2011 | Goldman et al. |
| 8,058,771 B2 | | 11/2011 | Giordano et al. |
| 8,073,531 B2 | | 12/2011 | Goldman et al. |
| 8,118,206 B2 | | 2/2012 | Zand et al. |
| 8,123,745 B2 | | 2/2012 | Beeckler et al. |
| 8,150,500 B2 | | 4/2012 | Goldman et al. |
| 8,244,333 B2 | | 8/2012 | Wood et al. |
| 8,255,040 B2 | | 8/2012 | Goldman et al. |
| 8,295,904 B2 | | 10/2012 | Goldman et al. |
| 8,380,291 B2 | | 2/2013 | Wood et al. |
| 8,391,960 B2 | | 3/2013 | Wood et al. |
| 8,417,306 B2 | | 4/2013 | Cheng |
| 8,463,364 B2 | | 6/2013 | Wood et al. |
| 8,467,857 B2 | | 6/2013 | Kim et al. |
| 8,478,386 B2 | | 7/2013 | Goldman et al. |
| 8,483,805 B2 | | 7/2013 | Takenoshita et al. |
| 8,483,819 B2 | | 7/2013 | Choi et al. |
| 8,489,178 B2 | | 7/2013 | Wood et al. |
| 8,586,924 B2 | | 11/2013 | Demos |
| 8,649,568 B2 | | 2/2014 | Sato |
| 8,649,848 B2 | | 2/2014 | Crane et al. |
| 8,682,418 B2 | | 3/2014 | Tanaka |
| 8,706,200 B2 | | 4/2014 | Goldman et al. |
| 8,712,498 B2 | | 4/2014 | Goldman et al. |
| 8,750,970 B2 | | 6/2014 | Goldman et al. |
| 8,792,967 B2 | | 7/2014 | Sato |
| 8,818,493 B2 | | 8/2014 | Goldman et al. |
| 8,838,210 B2 | | 9/2014 | Wood et al. |
| 8,900,219 B2 | * | 12/2014 | Sinofsky .............. A61B 5/7264 606/2 |
| 9,526,921 B2 | | 12/2016 | Kimball et al. |
| 2002/0169381 A1 | | 11/2002 | Asada et al. |
| 2003/0036685 A1 | | 2/2003 | Goodman |
| 2003/0036751 A1 | | 2/2003 | Anderson et al. |
| 2003/0120306 A1 | | 6/2003 | Burbank et al. |
| 2004/0111085 A1 | | 6/2004 | Singh |
| 2005/0143662 A1 | | 6/2005 | Marchitto et al. |
| 2005/0180620 A1 | | 8/2005 | Takiguchi |
| 2006/0020212 A1 | | 1/2006 | Xu et al. |
| 2006/0052850 A1 | | 3/2006 | Darmos et al. |
| 2006/0100523 A1 | | 5/2006 | Ogle et al. |
| 2006/0155194 A1 | | 7/2006 | Marcotte et al. |
| 2007/0038118 A1 | | 2/2007 | DePue et al. |
| 2009/0018414 A1 | | 1/2009 | Toofan |
| 2009/0054908 A1 | * | 2/2009 | Zand .................. A61B 5/0071 606/130 |
| 2010/0222786 A1 | | 9/2010 | Kassab |
| 2010/0249763 A1 | | 9/2010 | Larson et al. |
| 2011/0021925 A1 | | 1/2011 | Wood et al. |
| 2011/0245685 A1 | | 10/2011 | Murata et al. |
| 2012/0016362 A1 | | 1/2012 | Heinrich et al. |
| 2012/0046555 A1 | | 2/2012 | Takamatsu et al. |
| 2012/0143182 A1 | | 6/2012 | Ullrich et al. |
| 2012/0172842 A1 | | 7/2012 | Sela et al. |
| 2012/0296205 A1 | * | 11/2012 | Chernov .............. A61B 90/30 600/431 |
| 2012/0316448 A1 | * | 12/2012 | Gu .................. A61B 5/02108 600/499 |
| 2013/0102905 A1 | | 4/2013 | Goldman et al. |
| 2013/0131475 A1 | * | 5/2013 | Eisen .................. A61B 5/14552 600/324 |
| 2013/0226013 A1 | * | 8/2013 | McEwen .............. A61B 17/135 600/493 |
| 2013/0267874 A1 | | 10/2013 | Marcotte et al. |
| 2014/0086459 A1 | | 3/2014 | Pan et al. |
| 2014/0100455 A1 | | 4/2014 | Goldman et al. |
| 2014/0155753 A1 | | 6/2014 | McGuire, Jr. et al. |
| 2014/0194751 A1 | | 7/2014 | Goldman et al. |
| 2014/0236019 A1 | | 8/2014 | Rahum |
| 2014/0276088 A1 | | 9/2014 | Drucker |
| 2014/0276120 A1 | * | 9/2014 | Starr .................. A61B 5/0205 600/480 |
| 2014/0313482 A1 | | 10/2014 | Shahidi et al. |
| 2014/0343383 A1 | | 11/2014 | Sato |
| 2015/0011896 A1 | | 1/2015 | Yelin et al. |
| 2015/0051460 A1 | | 2/2015 | Saxena et al. |
| 2015/0066000 A1 | | 3/2015 | An et al. |
| 2015/0105638 A1 | * | 4/2015 | Eisen .................. A61B 5/14552 600/324 |
| 2016/0089198 A1 | * | 3/2016 | Arya .................. A61B 5/0075 600/317 |
| 2017/0181701 A1 | | 6/2017 | Fehrenbacher et al. |
| 2018/0098705 A1 | | 4/2018 | Chaturvedi et al. |

FOREIGN PATENT DOCUMENTS

| | | |
|---|---|---|
| JP | H10-005245 | 1/1998 |
| JP | 2003-019116 | 1/2003 |
| JP | 2006-325766 | 12/2006 |
| JP | 2007-252767 | 10/2007 |
| JP | 2010-081972 | 4/2010 |
| JP | 2013-121420 | 6/2013 |
| WO | WO98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |

(56) References Cited

FOREIGN PATENT DOCUMENTS

| WO | WO2008/082992 | 7/2008 |
| WO | WO2009/144653 | 12/2009 |
| WO | WO2011/013132 | 2/2011 |
| WO | WO2012/158774 | 11/2012 |
| WO | WO2013/134411 | 9/2013 |
| WO | WO2014/194317 | 12/2014 |
| WO | WO2015/148504 | 10/2015 |
| WO | WO2016/134330 | 8/2016 |
| WO | WO2017/062720 | 4/2017 |
| WO | WO2017/139624 | 8/2017 |
| WO | WO2017/139642 | 8/2017 |
| WO | WO2018/044722 | 3/2018 |

OTHER PUBLICATIONS

Shi, Ping, Vicente Azorin-Peris, Angelos Echiadis, Jia Zheng, Yisheng Zhu, Peck-Yeng Cheang and Sijung Hu. "Non-contact Reflection Photoplethysmography towards Effective Human Physiological Monitoring." (2010) (Year: 2010).*

International Search Report and Written Opinion, counterpart PCT application PCT/US2016/018798, 11 pages (dated May 11, 2016).

Akl et al., Performance Assessment of an Opto-Fluidic Phantom Mimicking Porcine Liver Parenchyma, J. Bio. Optics, vol. 17(7) 077008-1 to 077008-9 (Jul. 2012).

Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).

Ibey et al., Processing of Pulse Oximeter Signals Using Adaptive Filtering and Autocorrelation to Isolate Perfusion and Oxygenation Components, Proc SPIE, vol. 5702, 54-60 (2005).

Li et al., Pulsation-Resolved Deep Tissue Dynamics Measured with Diffusing-Wave Spectroscopy, Optics Express, vol. 14, No. 17, 7841-7851 (Aug. 21, 2006).

Mendelson et al., In-vitro Evaluation of a Dual Oxygen Saturation/Hematocrit Intravascular Fiberoptic Catheter, Biomed Instrum. Technol. 24(3):199-206 (May/Jun. 1990).

Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).

Subramanian, Real Time Perfusion and Oxygenation Monitoring in an Implantable Optical Sensor, Thesis Texas A&M Univ. (Dec. 2004).

Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).

Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

* cited by examiner

SYSTEM FOR DETERMINING VESSEL SIZE USING LIGHT ABSORPTION

The present application is a U.S. National Stage of PCT International Patent Application No. PCT/US2016/018798, filed on Feb. 19, 2016, which claims priority to Provisional Patent Application No. 62/118,429, filed Feb. 19, 2015, both of which are hereby incorporated herein by reference.

BACKGROUND

This patent is directed to a system and method for determining the size of a vessel, such as a blood vessel, and in particular to a system and method using the absorption of light for determining the size of a vessel, such as a blood vessel.

Systems and methods that identify artifacts, and in particular vessels, in the surgical field during a surgical procedure provide valuable information to the surgeon or surgical team. U.S. hospitals lose billions of dollars in unreimbursable costs because of inadvertent vascular damage during surgery. In addition, the involved patients face a mortality rate of up to 32%, and likely will require corrective procedures and remain in the hospital for an additional nine days, resulting in tens, if not hundreds, of thousands of dollars in added costs of care. Consequently, there is this significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally-invasive surgical procedures. Traditionally, surgeons have relied upon tactile sensation during surgical procedures both to identify blood vessels and to avoid inadvertent damage to these vessels. Because of the shift towards minimally-invasive procedures, including laparoscopic and robotic surgeries, surgeons have lost the ability to use the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity).

While the ability to determine the presence or absence of a vessel within the surgical field would provide valuable advantages to the surgeon or surgical team and is of particular importance for minimally-invasive procedures where tactile methods of identification have been lost, the ability to characterize the identified vasculature would provide additional important advantages. For example, it would be advantageous to provide information relating to the size of the vessel, such as the inner or outer diameter of the vessel.

In addition, it would be preferable to provide this information with minimal delay between vessel detection and vessel analysis, such that the information may be characterized as real-time. If considerable time is required for analysis, then at a minimum this delay will increase the time required to perform the procedure. In addition, the delay may increase surgeon fatigue, because the surgeon will be required to move at a deliberate pace to compensate for the delay between motion of the instrument and delivery of the information. Such delays may in fact hinder adoption of the system, even if the information provided reduces the risk of vascular injury.

Further, it would be advantageous to detect and analyze the vasculature without the need to use a contrast medium or agent. While the use of a contrast agent to identify vasculature has become conventional, the use of the agent still adds to the complexity of the procedure. The use of the agent may require additional equipment that would not otherwise be required, and increase the medical waste generated by the procedure. Further, the use of the contrast agent adds a risk of adverse reaction by the patient.

As set forth in more detail below, the present disclosure describes a surgical system including a vessel detector and method for determining vessel size embodying advantageous alternatives to the existing methods, which may provide for improved identification for avoidance or isolation of the vessel.

SUMMARY

According to an aspect of the present disclosure, a surgical system used to determine a size of a vessel within a region proximate to a working end of a surgical instrument includes at least one light emitter disposed at the working end of the surgical instrument, and at least one light sensor disposed at the working end of the surgical instrument opposite the at least one light emitter, the at least one light sensor adapted to generate a signal comprising a first pulsatile component and a second non-pulsatile component. The system also includes a controller coupled to the at least one light sensor, the controller comprising a splitter to separate the first pulsatile component from the second non-pulsatile component and an analyzer to quantify the size of the vessel within the region proximate to the working end of the surgical instrument based on the first pulsatile component.

According to another aspect of the present disclosure, a method of determining a size of a vessel within a region proximate to a working end of a surgical instrument includes emitting light at the working end of the surgical instrument, sensing light at the working end of the surgical instrument, and generating a signal having a first pulsatile component and a second non-pulsatile component based on the light sensed at the working end of the surgical instrument. The method also includes determining a size of a vessel within a region proximate to the working end of the surgical instrument based on the first pulsatile component of the signal.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

A surgical system according to an embodiment of the present disclosure includes at least one light emitter, at least one light sensor, and a controller. The system may also include a surgical instrument as well.

The system determines a size of a vessel within a region proximate to a working end of the surgical instrument. In particular, it is believed that the system may be used to determine the size of a vessel within the region proximate to the working end of the surgical instrument regardless of the presence or the type of tissue surrounding the vessel. The embodiments of the system described below perform determinations relative to the presence and size of the vessel within the targeted region based on the light transmittance as determined by the light sensor, and thus the embodiments may appear facially similar to the technology used in transmissive pulse oximetry to determine the oxygen saturation (i.e., the percentage of blood that is loaded with oxygen). Careful consideration of the following disclosure will reveal that disclosed system utilizes the light emitter(s) and light sensor(s) in conjunction with a controller (either in the form of unique circuitry or a uniquely programmed processor) to provide information regarding the presence and size of vessels that would not be provided by a pulse oximeter. Moreover, the disclosed technology may be utilized with vessels other than blood vessels, further separating the disclosed system and method from a transmissive pulse oximeter.

Figure 1:
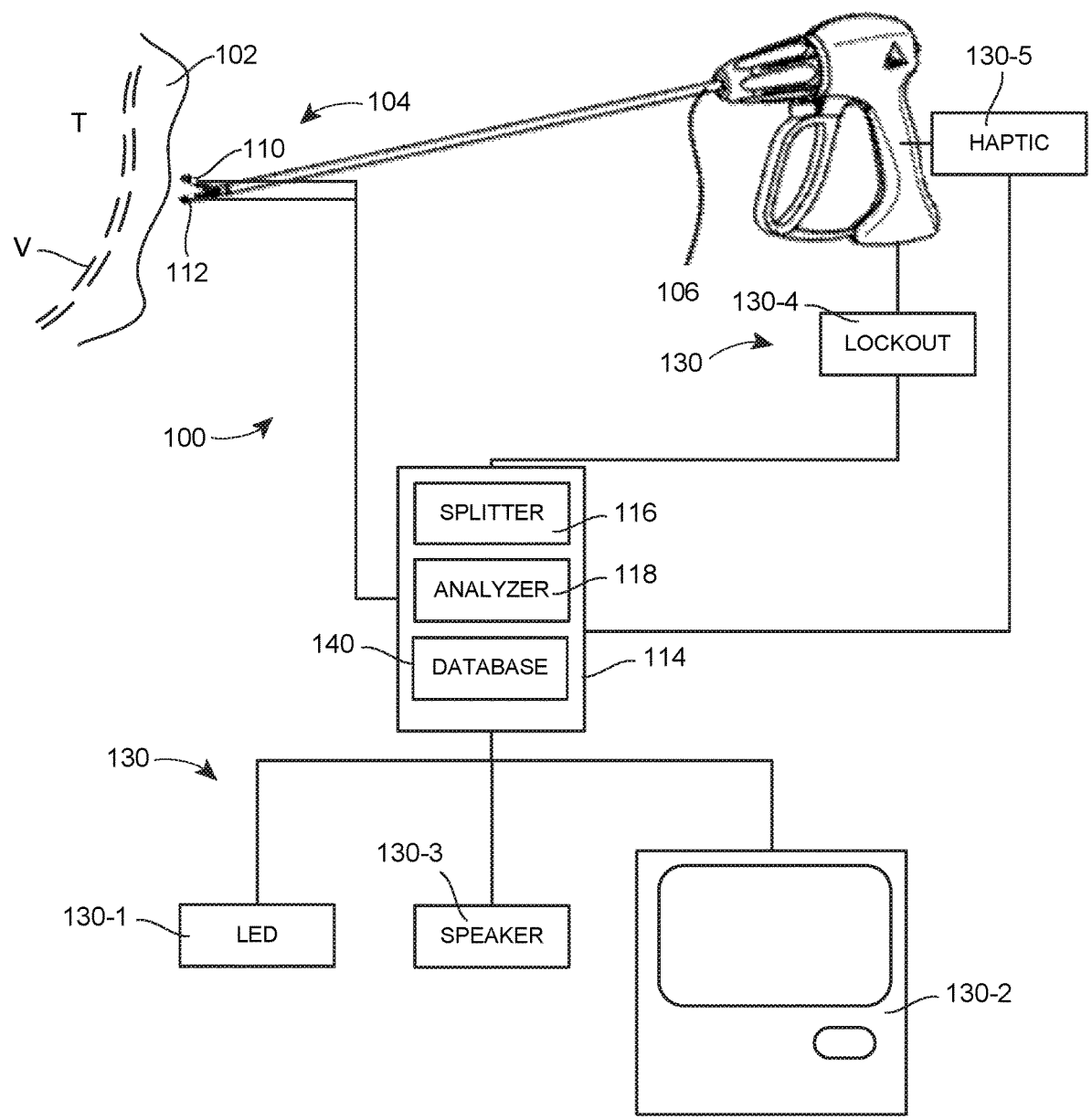
FIG. 1 is a schematic diagram of a surgical system according to an embodiment of the present disclosure.

FIG. 1 illustrates an embodiment of such a surgical system 100 used to determine a size (e.g., diameter) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIG. 1 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue or liver tissue.

The surgical system 100 includes at least one light emitter 110 (or simply the light emitter 110), at least one light sensor or detector 112 (or simply the light sensor 112), and a controller 114 coupled to the light emitter 110 and the light sensor 112. As noted above, the system 100 also may include the surgical instrument 106.

The light emitter 110 is disposed at the working end 104 of the surgical instrument 106. The light sensor 112 is also disposed at the working end 104 of the surgical instrument 106. As illustrated, the light sensor 112 may be disposed opposite the light emitter 110 because the light emitter 110 and the light sensor 112 are disposed on opposing elements of the surgical instrument 106, as explained in detail below.

The light emitter 110 is adapted to emit light of at least one wavelength. For example, the light emitter 110 may emit light having a wavelength of 940 nm. This may be achieved with a single element, or a plurality of elements (which elements may be arranged or configured into an array, for example, as explained in detail below). In a similar fashion, the light sensor 112 is adapted to detect light at the at least one wavelengths (e.g., 940 nm). This may also be achieved with a single element, or a plurality of elements (which elements may be arranged or configured into an array, for example).

In fact, the light emitter 110 may be configured to emit light of at least two different wavelengths, and the light sensor 112 may be configured to detect light at the at least two different wavelengths. For example, the light emitter 110 may emit light of three wavelengths, while the light sensor may detect light of three wavelengths. As one example, the light emitter 110 may emit and the light sensor 112 may detect light in the visible range, light in the near-infrared range, and light in the infrared range. Specifically, the light emitter 110 may emit and the light sensor 112 may detect light at 660 nm, at 810 nm, and at 940 nm. Such an embodiment may be used, for example, to ensure optimal penetration of blood vessel V and the surrounding tissue T under in vivo conditions.

Figure 2:
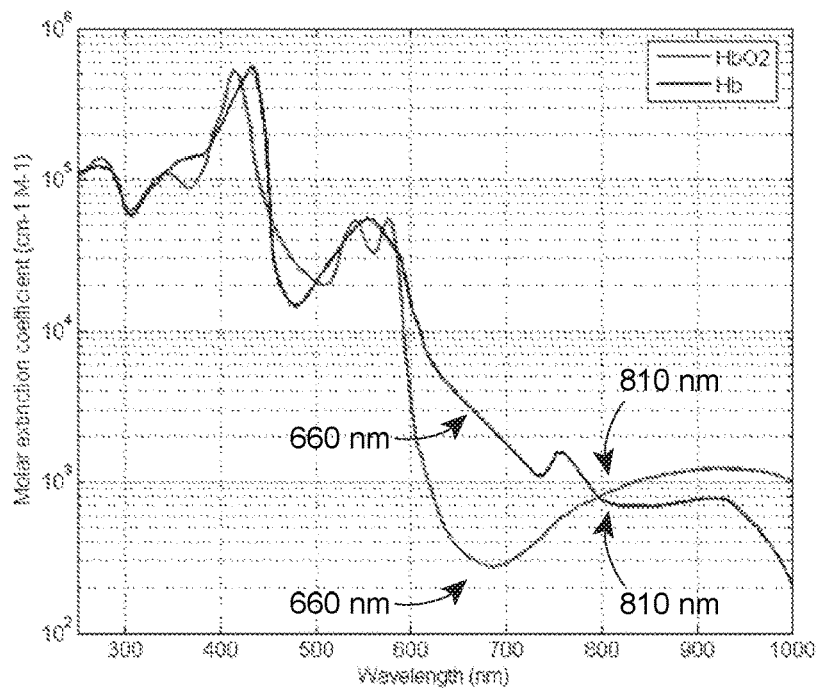
FIG. 2 is a chart showing the light absorption of blood.

In particular, the light emitted at 810 nm may be used as a reference to remove any variations in the light output because of motion and/or blood perfusion. The 810 nm wavelength corresponds to the isobestic point, where the absorption for both oxygenated and deoxygenated hemoglobin is equal (see FIG. 2). Consequently, the absorption at this wavelength is independent of blood oxygenation and is only affected by the change in light transmittance because of motion and/or changes in perfusion.

According to the embodiments of this disclosure, the light sensor 112 is adapted to generate a signal comprising a first pulsatile component and a second non-pulsatile component. It will be recognized that the first pulsatile component may be an alternating current (AC) signal component of the signal, while the second non-pulsatile component may be a direct current (DC) signal component.

For example, a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 112 will produce a signal (that is passed to the controller 114) with a particular AC waveform that corresponds to the movement of the blood through the vessel. In particular, the AC waveform corresponds to the light absorption by the pulsatile blood flow within the vessel. On the other hand, the DC component corresponds principally to light absorption and scattering by the surrounding tissues.

The controller 114 is coupled to the light sensor 112, and incudes a splitter 116 to separate the first pulsatile component from the second non-pulsatile component. The controller 114 also includes an analyzer 118 to quantify the size of the vessel V within the region 102 proximate to the working end 104 of the surgical instrument 106 based on the first pulsatile component. To display, indicate or otherwise convey the size of the vessel V within the region 102, the controller 114 may be coupled to an output device or indicator 130, which may provide a visible, audible, tactile or other signal to the user of the instrument 106.

According to certain embodiments, the splitter 116 and the analyzer 118 may be defined by one or more electrical circuit components. According to other embodiments, one or more processors (or simply the processor) may be programmed to perform the actions of the splitter 116 and the analyzer 118. According to still further embodiments, the splitter 116 and the analyzer 118 may be defined in part by electrical circuit components and in part by a processor programmed to perform the actions of the splitter 116 and the analyzer 118.

For example, the splitter 116 may include or be defined by the processor programmed to separate the first pulsatile component from the second non-pulsatile component. Further, the analyzer 118 may include or be defined by the processor programmed to quantify the size of the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

According to the embodiments of the system 100, the analyzer 118 may quantify the size of the vessel according to a magnitude of the first component of the signal from the at least one light sensor 112. In fact, according to certain embodiments, the analyzer 118 quantifies the size of the vessel according to a ratio of the magnitude of the first component to a magnitude of the second component. More particularly, the analyzer 118 may quantify the size of the vessel according to a ratio of the logarithm of the magnitude of the first component and the logarithm of the magnitude of the second component. It is believed that the system 100 quantifies the size of the blood vessel regardless of the type or thickness of the tissue surrounding the vessel.

According to some embodiments, the analyzer 118 may compare the magnitude of the first component, the ratio of the magnitudes of the first and second components, or the ratio of the ratio of the logarithms of the magnitudes of the first and second components to a database or look-up table 140 of magnitudes and vessel sizes. The database/table 140 may be generated based on experimental data wherein the system 100 is used to determine the relationship between various ratios of the magnitudes of the first and second components (or more particularly, between various ratios of or ratios of the logarithms of the first and second components) and vessel sizes, the vessel sizes being positively determined after the data has been collected using the system 100 by cross-sectioning of the vessels and microscopic analysis.

In addition to the system 100, the present disclosure includes embodiments of a method 150 of determining if a size of a vessel V within a region 102 proximate to a working end 104 of a surgical instrument 106. The method 150 may be carried out, for example, using a system 100 as described above in regard to FIG. 1.

Figure 3:
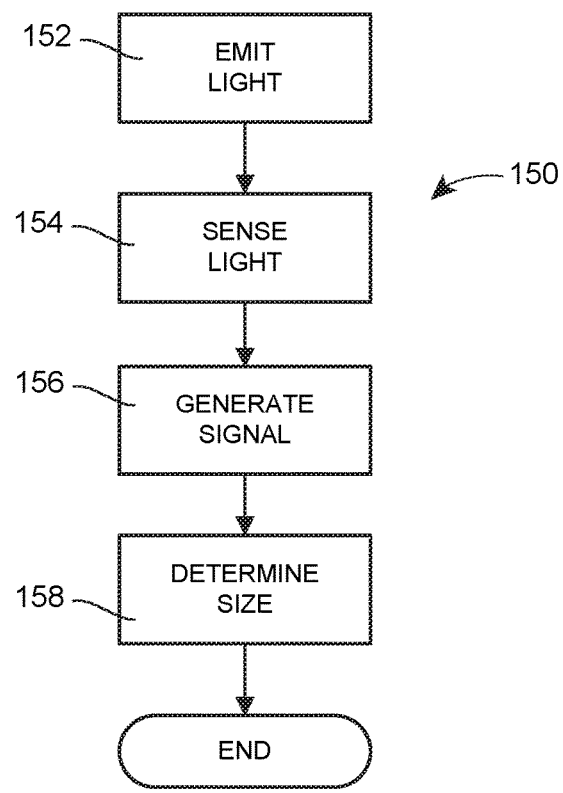
FIG. 3 is a flow diagram of a method of determining a size of a vessel within a region proximate to a working end of a surgical instrument according to an embodiment of the present disclosure, which method may be carried out using the system of FIG. 1.

As reflected in the flowchart of FIG. 3, the method 150 includes emitting light at the working end of the surgical instrument (block 152), sensing light at the working end of the surgical instrument (block 154), and generating a signal having a first pulsatile component and a second non-pulsatile component based on the light sensed at the working end of the surgical instrument (block 156). The method 150 may also include determining a size of a vessel within a region proximate to the working end of the surgical instrument based on the first pulsatile component of the signal (block 158).

Figure 4:
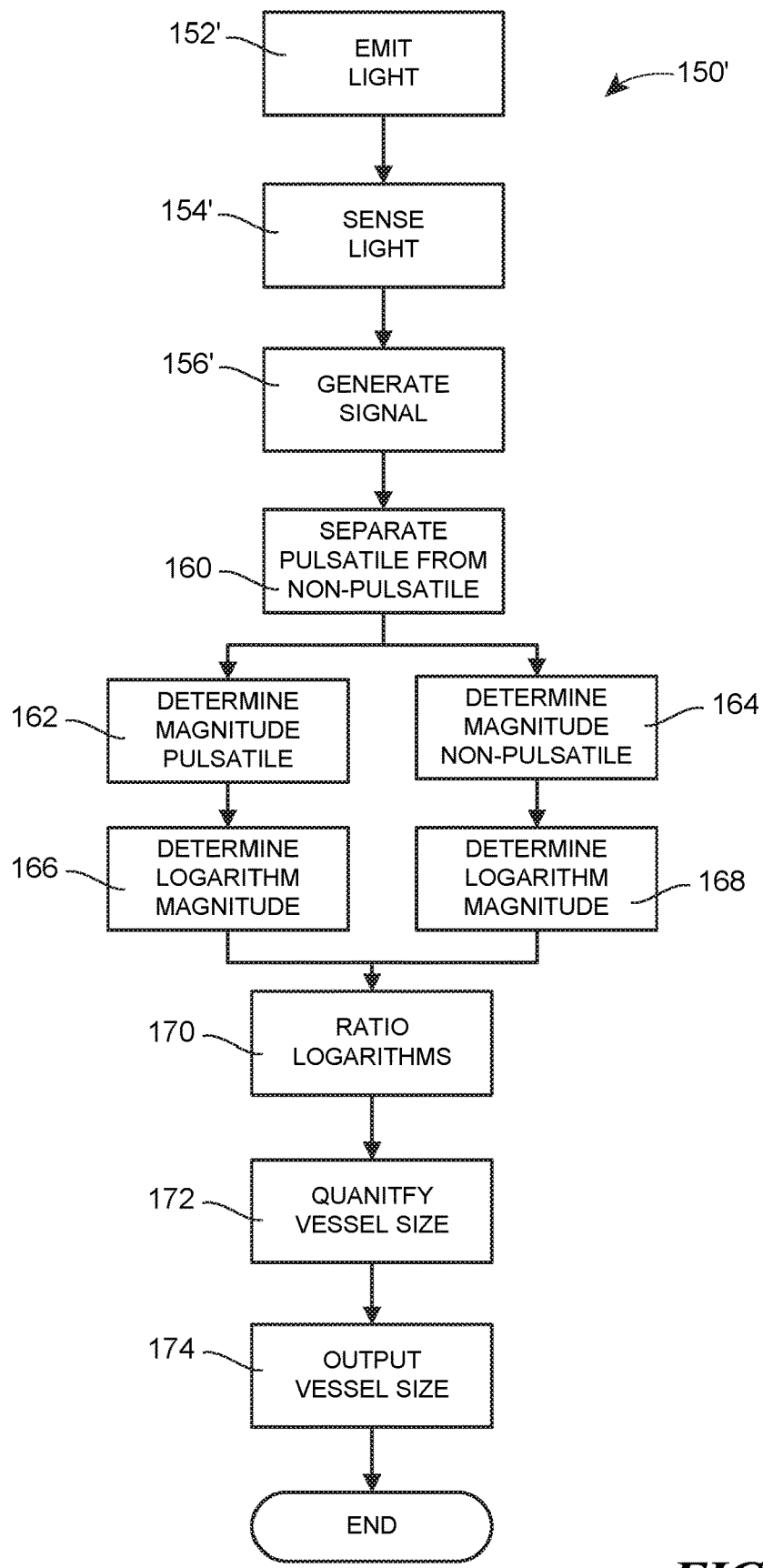
FIG. 4 is a flow diagram of a method according to an additional embodiment of the present disclosure, which method may be carried out using the system of FIG. 1.

A further embodiment of the method is illustrated in FIG. 4. According to this embodiment, a method 150' includes emitting light at the working end of the surgical instrument (block 152'), sensing light at the working end of the surgical instrument (block 154'), and generating a signal having a first pulsatile component and a second non-pulsatile component based on the light sensed at the working end of the surgical instrument (block 156'). Because these actions are common to the methods 150, 150', similar reference numerals have been used, with the elements of the method 150' of FIG. 3 being indicated with the inclusion of a prime.

According to the method 150', determination of the size of the vessel may include determining the size of the vessel within the region proximate to the working end of the surgical instrument according to a magnitude of the first pulsatile component of the signal. The determination of the size of the vessel according to method 150' may further include determining the size of the vessel within the region proximate to the working end of the surgical instrument according to a ratio of a magnitude of the first pulsatile component to a magnitude of the second component. Further, determination of the size of the vessel according to method 150' may also include comparing the ratio of the magnitudes of the first and second components to a database of magnitudes and vessel sizes. According to other embodiments, the method of determining the size of the vessel may include fewer than all of these actions.

As illustrated, the method 150' includes separating the first pulsatile component from the second non-pulsatile component (block 160). Further, the method 150' includes determining the magnitude of the first component (block 162) and determining the magnitude of the second component (block 164). In addition, the method 150' includes determining the logarithm of the magnitude of the first component (block 166) and the logarithm of the magnitude of the second component (block 168). It will be recognized that blocks 160, 162, 164, 166 may be performed sequentially instead of in parallel.

Further, the method 150' includes determining the ratio of the logarithms of the magnitudes of the first and second components (block 170) and quantifying the size of the vessel V based on the ratio of the logarithms of the magnitudes of the first and second components (block 172). As mentioned above, block 172 may include the action of comparing the ratio to a database or look-up table. The method 150' also includes providing an output via the indicator 130 (block 174).

As explained above, the light emitted may include light of at least two different wavelengths, and the sensing step may thus include sensing light of at least two different wavelengths. As also noted above, three different wavelengths of light may be used, and for example in the visible range and the near-infrared range. According to one embodiment, the light used may have wavelengths of 660 nm, 810 nm, and 940 nm.

Having thus described the surgical system 100, the method 150, 150' and the principles of the system 100 and the method 150, 150' in general terms, further details of the system 100 and its operation are provided.

Initially, while the emitter 110 and the sensor 112 are described as disposed at the working end 104 of the surgical instrument 106, it will be recognized that not all of the components that define the emitter 110 and the sensor 112 need be disposed at the working end of the instrument 106. That is, the emitter 110 may comprise a light emitting diode, and that component may be disposed at the working end 104. Alternatively, the emitter 110 may include a length of optical fiber and a light source, the source disposed remotely from the working end 104 and the fiber having a first end optically coupled to the source and a second end disposed at the working end 104 facing the sensor 112. According to the present disclosure, such an emitter 110 would still be described as disposed at the working end 104 because the light is emitted into the tissue at the working end 104 of the instrument 106. A similar arrangement may be described for the sensor 112 wherein an optical fiber has a first end disposed facing the emitter 110 (or perhaps more particularly, an end of the optical fiber that in part defines the emitter 110) and a second end optically coupled to other components that collectively define the sensor 112.

Figure 5:
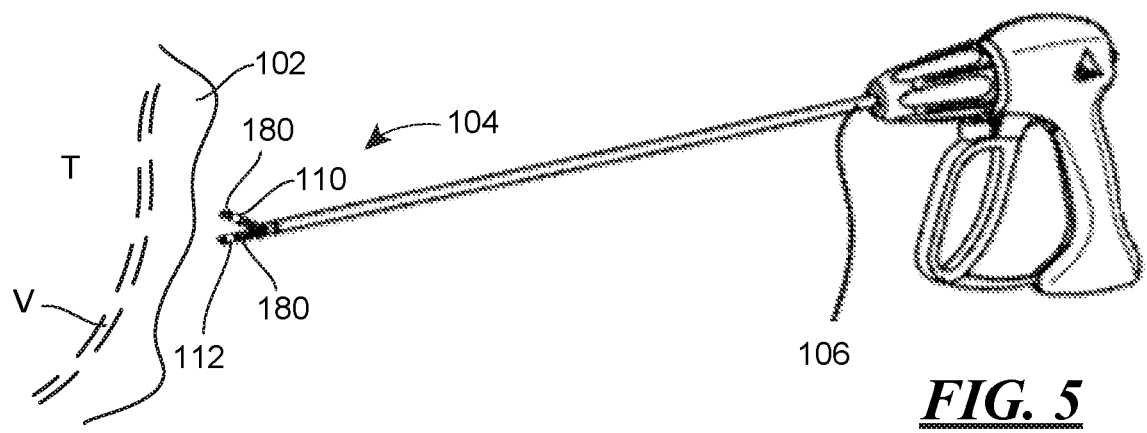
FIG. 5 is a schematic of a surgical instrument with light emitters and light sensors according to an embodiment of the present disclosure.

As also mentioned above, the light emitter 110 and light sensor 112 are positioned opposite each other. This does not require the emitter 110 and the sensor 112 to be directly facing each other, although this is preferred. According to certain embodiments, the emitter 110 and sensor 112 may be formed integrally (i.e., as one piece) with jaws 180 of a surgical instrument 106. See FIGS. 1, 4 and 5. In this manner, light emitted by the emitter 110 between the jaws 180 and through the tissue of interest may be captured by the light sensor 112.

Figure 6:
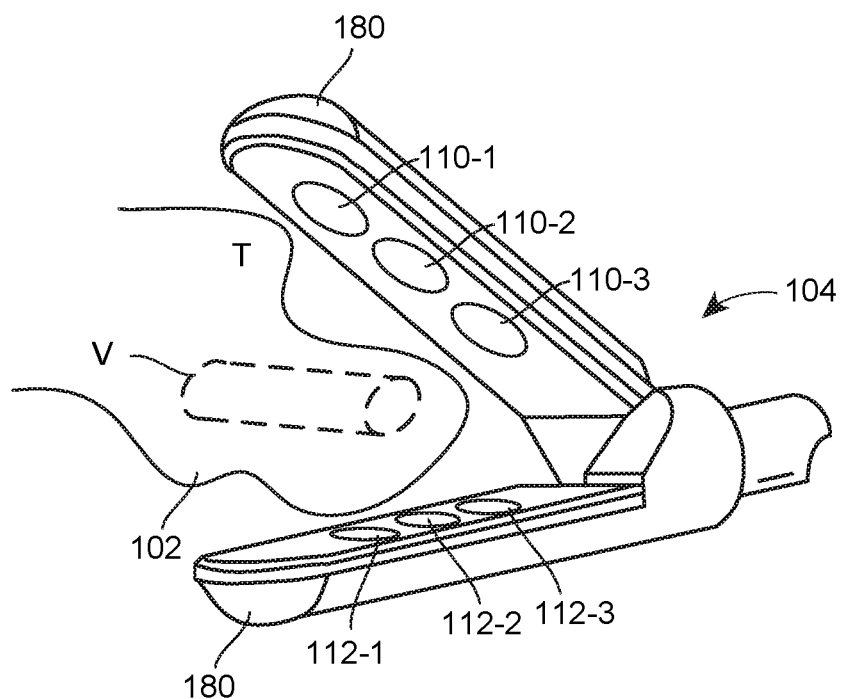
FIG. 6 is an enlarged, fragmentary view of the surgical instrument with light emitter and light sensors according to FIG. 5 with a section of an vessel illustrated as disposed between the light emitter and light sensors.

The light emitter 110 may include one or more elements. According to an embodiment schematically illustrated in FIGS. 5 and 6, the light sensor 112 may include a first light emitter 110-1, a second light emitter 110-2, and a third light emitter 110-3. The first light emitter 110-1 may be adapted to emit light in the visible range, the second light emitter 110-2 may be adapted to emit light in the near-infrared range, and the third light emitter 110-3 may be adapted to emit light in the infrared range. For example, the first light emitter 110-1 may be adapted to emit light at 600 nm or 660 nm, the second light emitter 110-2 may be adapted to emit light at 810 nm, and the third light emitter 110-3 may be adapted to emit light at 940 nm.

As to those embodiments wherein the light emitter 110 is in the form of one or more light emitting diodes, for example, disposed at the working end 104 of the instrument 106, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 112 may also include one or more elements. According to an embodiment schematically illustrated in FIGS. 5 and 6, the light sensor 112 may include a first light sensor 112-1, a second light sensor 112-2, and a third light sensor 112-3. The first light sensor 112-1 may be adapted to detect light in the visible range, the second light sensor 112-2 may be adapted to detect light in the near-infrared range, and the third light sensor 112-3 may be adapted to detect light in the infrared range. For example, the first light sensor 112-1 may be adapted to detect light at 600 nm or 660 nm, the second light sensor 112-2 may be adapted to detect light at 810 nm, and the third light sensor 112-3 may be adapted to detect light at 940 nm. According to other embodiments, each sensor 112-1, 112-2, 112-3 may be capable of detecting light at all three wavelengths. As was the case with the light emitters 110-1, 110-2, 110-3, the light sensors 112-1, 112-2, 112-3 may be arranged in an array, and the discussion in regard to the arrays above applied with equal force here.

As discussed above, the system 100 may include hardware and software in addition to the emitter 110, sensor 112, and controller 114. For example, where more than one emitter 110 is used, a drive controller may be provided to control the switching of the individual emitter elements. In a similar fashion, a multiplexer may be provided where more than one sensor 112 is included, which multiplexer may be coupled to the sensors 112 and to an amplifier. Further, the controller 114 may include filters and analog-to-digital conversion as may be required.

As for the indicator 130 used in conjunction with controller 114, a variety of output devices may be used. For example, a light emitting diode 130-1 may be attached to or incorporated into the associated surgical instrument 106, and may even be disposed at the working end 104 of the instrument 106. Alternatively, an alert may be displayed on a video monitor 130-2 being used for the surgery, or may cause an image on the monitor to change color or to flash, change size or otherwise change appearance. The indicator 130 may also be in the form of or include a speaker 130-3 that provides an auditory alarm. The indicator 130 also may be in the form of or may incorporate a safety lockout 130-4 associated with the surgical instrument 106 that interrupts use of the instrument 106. For example, the lockout could prevent ligation or cauterization where the surgical instrument 106 is a thermal ligature device. As a still further example, the indicator 130 also may be in the form of a haptic feedback system, such as a vibrator 130-5, which may be attached to or formed integral with a handle or handpiece of the surgical instrument 106 to provide a tactile indication or alarm. Various combinations of these particular forms of the indicator 130 may also be used.

As mentioned above, the surgical system 100 may also include the surgical instrument 106 with the working end 104, to which the light emitter 110 and light sensor 112 are attached (in the alternative, removably or permanently/irreversibly). The light emitter 110 and the light sensor 112 may instead be formed integrally (i.e., as one piece) with the surgical instrument 106. It is further possible that the light emitter and light sensor be attached to a separate instrument or tool that is used in conjunction with the surgical instrument or tool 106.

As noted above, the surgical instrument 106 may be a thermal ligature device in one embodiment. According to other embodiments, the surgical instrument may be other surgical instruments such as dissectors, graspers or grasping forceps, surgical staplers, clip appliers, and robotic surgical systems, for example. The illustration of a single embodiment is not intended to preclude the use of the system 100 with other surgical instruments or tools 106.

EXAMPLES

A series of experiments have been conducted using an embodiment of the above-described system. The experiments and results are reported below.

The embodiment of the system used for the experiments included a single light emitter (a light emitting diode) and a single light sensor mounted in an adjustable test rig with the light sensor disposed across a test region opposite the light emitter. The rig included a frame or base (on which the light sensor was mounted), two straight guide rods attached to the frame (and spaced on either side of the test region) and a block (to which the light emitter was mounted) slideably mounted on the guide rods so that the block could be adjustably translated relative to the base. One of the guide rods was threaded so that the distance between the emitter and sensor could be better controlled.

To simulate the pulsatile flow of fluid found in vessels, such as blood vessels (e.g., arteries) for example, a submersible DC pump was used. The pump was capable of operation at between 40 and 80 cycles per minute, and could provide a flow rate that could be set to a particular value. The fluid used was bovine whole blood to which heparin had been added and that was maintained at an elevated temperature to maintain physiological viscosity. For the experiments described below, the blood was pumped at 60 cycles per minute and at a flow rate of 500 mL per minute.

To simulate the vessels in the first two groups of experiments, clear PVC tubes of varying inner diameters (4 mm, 4.8 mm, 6 mm, 8 mm) were disposed in the test region of the rig between the light emitter and the light sensor, while fluid was passed through the tubes. In the third group of experiments, skeletonized porcine carotid artery of varying inner diameters were used.

During the first group of experiments, the tubes were placed in the rig without any additional material between the light emitter/sensor pair and the tube. The pump was operated to pass blood through the tube, and measurements were taken of the pulsatile component of the signal from the sensor.

Figure 7:
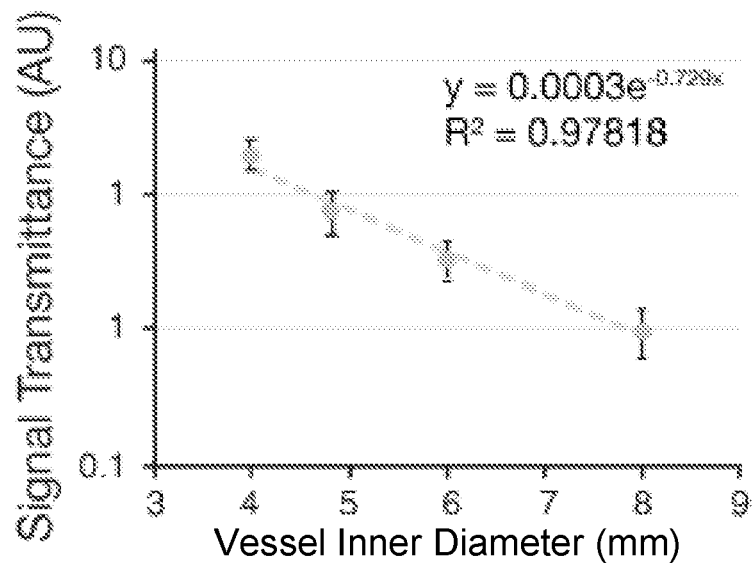
FIG. 7 is a graph of the transmittance values versus the vessel (tube) inner diameters for a first group of experiments.

FIG. 7 illustrates the correlation between the pulsatile component and the diameter of the tube. A direct correlation between the pulsatile component and the vessel size can be observed.

During the second group of experiments, the tubes were placed in the rig with the tubes wrapped with (surrounded by) various types of porcine tissue. In particular, porcine adipose tissue, a combination of porcine adipose and porcine connective tissue, and porcine liver tissue were used. Samples were prepared for each of four different tube inner diameters (4 mm, 4.8 mm, 6 mm, 8 mm) and each of the three different tissue types and a no-tissue control. In total, sixty samples were prepared and placed in the test rig for testing.

Figure 8:
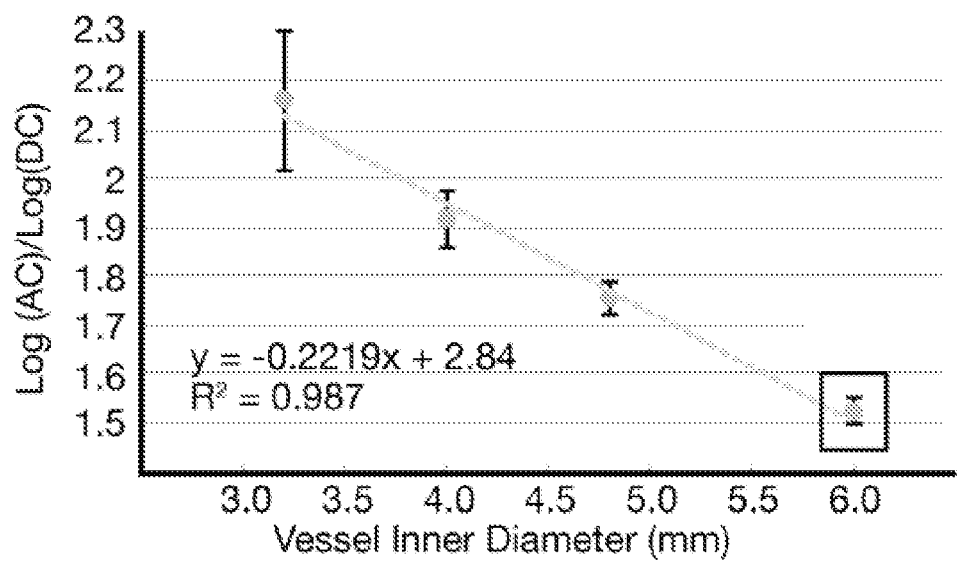
FIG. 8 is a graph of the ratios of the logarithms of the pulsatile and non-pulsatile components of the transmittance signal versus the vessel (tube) inner diameters for a second group of experiments, the vessels having been wrapped with four different tissue types (no-tissue, adipose tissue, connective and adipose tissue, and liver tissue)
Figure 9:
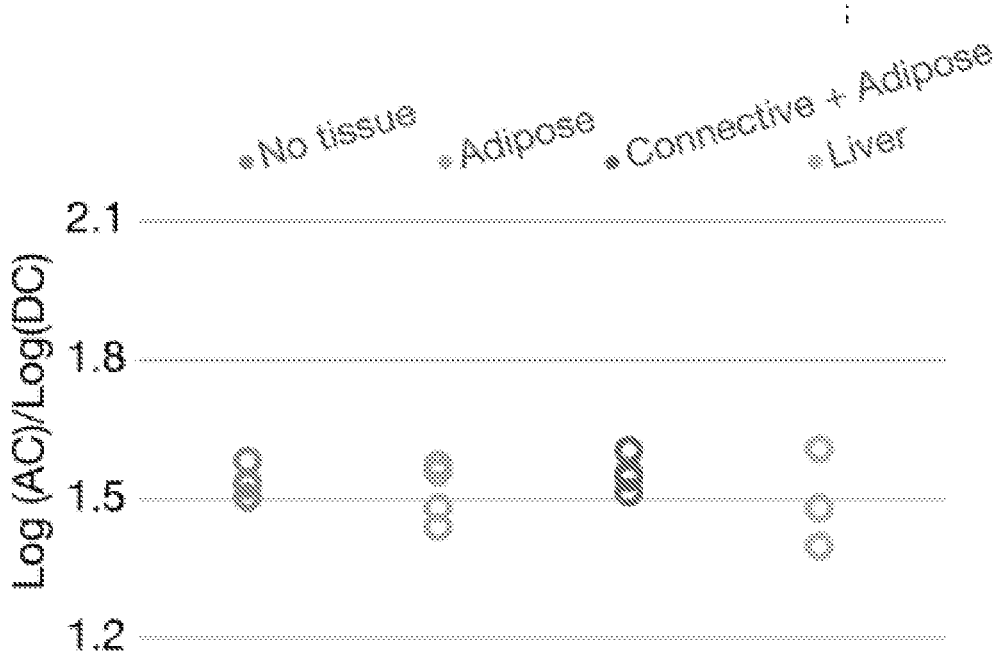
FIG. 9 is a graph of the ratio of the logarithms of the pulsatile and non-pulsatile components of the transmittance signal for a vessel having an inner diameter of 6 mm wrapped in different types of tissue (each column representing a different tissue type)

FIG. 8 illustrates the correlation between the ratio of the logarithms of the pulsatile and non-pulsatile light transmittance signals for each diameter and the range of tissues (no-tissue, adipose, adipose and connective, liver), while FIG. 9 illustrates the correlation between the ratios calculated for different tissue types (no-tissue, adipose, connective/adipose, liver) for a vessel having an inner diameter of 6 mm. As seen in FIG. 8, regardless of the tissue type, the ratio correlated very well ($R^2=0.987$) with the vessel diameter. In addition, as seen in FIG. 9, the ratios calculated for the different tissue types were essentially the same, indicating that the metric (ratio) is independent of the surrounding tissue. Importantly, the varying tissue types and tissue thicknesses caused no different in the signal output according to ANOVA tests ($p>0.05$), indicating the specificity of the metric to vessel inner diameter.

During the third group of experiments, skeletonized porcine carotid arteries of varying inner diameter were placed in the rig without any additional material between the light emitter/sensor pair and the arteries. The pump was operated to pass blood through the artery, and measurements were taken of the pulsatile component of the signal from the sensor. The diameters of the vessels were obtained by quantifying the cross-section of the vessels at the point of measurement along the vessels using NIH ImageJ software.

Figure 10:
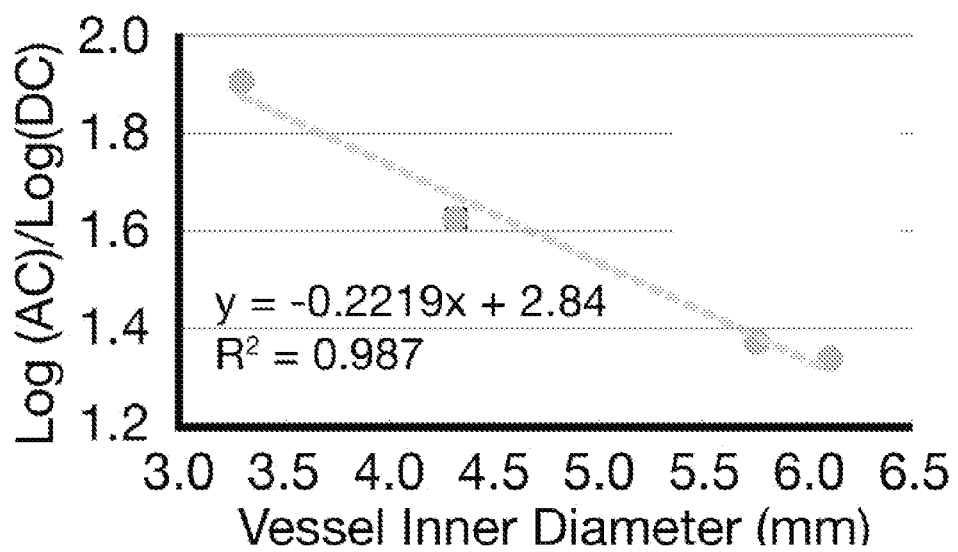
FIG. 10 is a graph of the ratio of the logarithms of the pulsatile and non-pulsatile components of the transmittance signal versus vessel inner diameters for a third group of experiments, the vessels being skeletonized porcine carotid arteries.

FIG. 10 illustrates the correlation between the ratio of the logarithms of the pulsatile and non-pulsatile light transmittance signals for vessels of varying inner diameter. A correlation between the pulsatile component and the vessel size can be observed, with $R^2=0.987$.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system configured to determine a diameter of a vessel within a region proximate to a working end of a surgical instrument, comprising:

at least one light emitter disposed at the working end of the surgical instrument;

at least one light sensor disposed at the working end of the surgical instrument and opposite the at least one light emitter at the working end of the surgical instrument, the at least one light sensor configured to generate a signal comprising a first pulsatile component and a second non-pulsatile component; and a controller coupled to the at least one light sensor, the controller comprising a splitter configured to separate the first pulsatile component from the second non-pulsatile component and an analyzer configured to quantify the diameter of the vessel within the region proximate to the working end of the surgical instrument, wherein the analyzer is configured to quantify the diameter of the vessel according to a ratio of a magnitude of the first pulsatile component to a magnitude of the second non-pulsatile component.

2. The surgical system according to claim 1, wherein the analyzer is configured to compare the ratio of the magnitudes of the first pulsatile and second non-pulsatile components to a database of magnitudes and vessel diameters.

3. The surgical system according to claim 1, wherein the first pulsatile component comprises an alternating current signal component and the second non-pulsatile component comprises a direct current signal component.

4. The surgical system according to claim 1, wherein the controller comprises a processor and memory, and the splitter comprises the processor programmed to separate the first pulsatile component from the second non-pulsatile component and the analyzer comprises the processor programmed to quantify the size diameter of the vessel within the region proximate to the working end of the surgical instrument according to the ratio of the magnitude of the first component to the magnitude of the second component.

5. The surgical system according to claim 1, wherein the at least one light emitter is configured to emit light of at least three different wavelengths, and the at least one light sensor is configured to detect light at the at least three different wavelengths.

6. The surgical system according to claim 5, wherein the at least one light sensor is configured to detect light in the visible range, in the near-infrared range, and in the infrared range.

7. The surgical system according to claim 6, wherein the at least one light sensor is configured to detect light at wavelengths of 660 nm, at 810 nm and at 940 nm.

8. The surgical system according to claim 1, further comprising a surgical instrument having a working end.

9. The surgical system according to claim 8, wherein the surgical instrument comprises first and second opposing jaw elements, the at least one light emitter disposed on the first jaw element and the at least one light sensor disposed on the second, opposing jaw element.

10. The surgical system according to claim 8, wherein the surgical instrument is a grasper or a thermal ligature device.

11. A method of determining a diameter of a vessel within a region proximate to a working end of a surgical instrument, comprising:

emitting light at the working end of the surgical instrument;

sensing light at the working end of the surgical instrument;

generating a signal having a first pulsatile component and a second non-pulsatile component based on the light sensed at the working end of the surgical instrument; and determining a diameter of a vessel within a region proximate to the working end of the surgical instrument according to a ratio of a magnitude of the first pulsatile component to a magnitude of the second non-pulsatile component.

12. The method according to claim 11, wherein determining the diameter of the vessel comprises comparing the ratio of the magnitudes of the first pulsatile and second non-pulsatile components to a database of magnitudes and vessel sizes.

13. The method according to claim 11, further comprising separating the first pulsatile component from the second non-pulsatile component.

14. The method according to claim 11, wherein emitting light comprises emitting light of at least three different wavelengths, and wherein sensing light comprises sensing light of at least three different wavelengths.

15. The method according to claim 14, wherein sensing light comprises sensing light in the visible range, in the near-infrared range and in the infrared range.

16. The method according to claim 15, wherein the sensing light comprises sensing light at wavelengths of 660 nm, at 810 nm, and at 940 nm.

* * * * *